(12) United States Patent
Varineau et al.

(10) Patent No.: US 8,211,949 B2
(45) Date of Patent: Jul. 3, 2012

(54) FUNCTIONALIZED LONG-CHAIN OLEFIN MIXTURES AND USES THEREFOR

(75) Inventors: Pierre T. Varineau, Lake Jackson, TX (US); Brian W. Kolthammer, Lake Jackson, TX (US); Aaron W. Sanders, Missouri City, TX (US); David A. Wilson, Lake Jackson, TX (US); Kara S. Weber, Lake Jackson, TX (US); Robert Kirk Thompson, Lake Jackson, TX (US); Cynthia L. Rand, Sanford, MI (US); Thomas C. Eisenschmid, Cross Lanes, WV (US)

(73) Assignee: Dow Global Technologies LLC, Midland, MI (US)

( * ) Notice: Subject to any disclaimer, the term of this patent is extended or adjusted under 35 U.S.C. 154(b) by 807 days.

(21) Appl. No.: 12/211,583

(22) Filed: Sep. 16, 2008

(65) Prior Publication Data

US 2009/0078910 A1    Mar. 26, 2009

Related U.S. Application Data

(60) Provisional application No. 60/974,604, filed on Sep. 24, 2007.

(51) Int. Cl.
| | |
|---|---|
| *C09K 3/00* | (2006.01) |
| *C11D 1/12* | (2006.01) |
| *C11D 1/68* | (2006.01) |
| *C11D 1/722* | (2006.01) |
| *C11D 1/40* | (2006.01) |
| *C11D 1/825* | (2006.01) |
| *C07C 309/20* | (2006.01) |
| *C07C 209/24* | (2006.01) |
| *C07C 45/50* | (2006.01) |
| *C07C 27/20* | (2006.01) |
| *B01F 17/02* | (2006.01) |
| *B01F 17/16* | (2006.01) |
| *B01F 17/38* | (2006.01) |
| *B01F 17/32* | (2006.01) |
| *B01D 12/00* | (2006.01) |

(52) U.S. Cl. ........ 516/200; 516/203; 516/204; 516/909; 516/914; 516/920; 568/671; 568/700; 568/840; 568/884; 568/451; 564/471; 564/472; 564/473; 562/30; 562/120; 510/535; 510/536; 510/537

(58) Field of Classification Search .................. 516/204, 516/200, 203; 568/671, 700, 840, 876, 884, 568/909, 913, 451; 564/467, 471, 472, 473; 562/30, 120; 510/535, 536, 537
See application file for complete search history.

(56) References Cited

U.S. PATENT DOCUMENTS 2,695,327 A    11/1954   Ziegler et al.
(Continued)

FOREIGN PATENT DOCUMENTS

EP            958267            3/2004
(Continued)

OTHER PUBLICATIONS

K. Blann, et al., "Highly Selective Chromium-Based Ethylene Trimerisation Catalysts with Bulky Diphosphinoamine Ligands", Chem. Commun., 2005, 620-621, The Royal Society of Chemistry.

(Continued)

*Primary Examiner* — Daniel S Metzmaier

(57) ABSTRACT

Novel mixtures of long-chain (C10-C20) olefins are functionalized by conversion to aldehydes using an OXO process, or to sulfates, sulfonates, sulfones, sulfides, or sulfoxides by direct sulfonation. The aldehydes may then be hydrogenated to form alcohols, or aminated to form amines or amides. The olefins starting mixture may be acquired as a byproduct of the tetramerization of ethylene in the presence of certain chromium-containing tetramerization catalysts. The functionalized mixtures, and derivatives prepared therefrom such as alkoxylates prepared from the alcohols, may be useful as surfactants that may offer improved performance in many applications, while their preparation based on a byproduct mixture reduces their cost and also reduces waste-handling issues for this non-targeted stream.

11 Claims, 3 Drawing Sheets

Linear Isomers
20-45% Terminal Linear
1-15% Internal Linear

+ Other C10 Linear internal olefins

Branched Isomers
40-79%

U.S. PATENT DOCUMENTS

| | | | |
|---|---|---|---|
| 3,887,624 | A | 6/1975 | Gipson et al. |
| 3,952,068 | A | 4/1976 | Gipson et al. |
| 4,102,911 | A | 7/1978 | Majima et al. |
| 4,598,162 | A * | 7/1986 | Forster et al. ............... 568/448 |
| 5,780,694 | A | 7/1998 | Singleton |
| 5,780,698 | A * | 7/1998 | Baralt et al. ............... 585/521 |
| 5,849,960 | A | 12/1998 | Singleton et al. |
| 6,433,207 | B1 | 8/2002 | Connor |
| 6,482,789 | B1 | 11/2002 | Kvietok et al. |
| 6,963,014 | B1 | 11/2005 | Zeller et al. |
| 7,220,884 | B2 | 5/2007 | Briggs et al. |
| 7,297,832 | B2 * | 11/2007 | Blann et al. ............... 585/527 |
| 2004/0077894 | A1 * | 4/2004 | Edwards et al. ............... 558/38 |
| 2004/0133037 | A1 | 7/2004 | Fenouil et al. |
| 2005/0170991 | A1 | 8/2005 | Ruland et al. |
| 2005/0215792 | A1 * | 9/2005 | De Boer et al. ............... 546/2 |
| 2006/0235250 | A1 * | 10/2006 | De Boer et al. ............... 585/502 |
| 2007/0185357 | A1 * | 8/2007 | De Boer et al. ............... 585/511 |

FOREIGN PATENT DOCUMENTS

| | | |
|---|---|---|
| WO | WO 0042154 | 7/2000 |
| WO | WO 2004/056478 | 7/2004 |
| WO | WO 2007/057455 A1 * | 5/2007 |
| WO | WO 2007/057458 A1 * | 5/2007 |

OTHER PUBLICATIONS

A. Bollmann, et al., "Ethylene Tetramerization: A New Route to Produce 1-Octene in Exceptionally High Selectivities," Journal of the American Chemical Society, 2004, 14712-14713, vol. 126, No. 45, American Chemical Society.

G.R. Lappin, et al., "Olefins, Higher", Kirk-Othmer Encyclopedia of Chemical Technology (online edition), 1996, 709-728, vol. 17, John Wiley & Sons, Inc. Article Online Posting Date Dec. 4, 2000.

M. J. Overett, et al., "Mechanistic Investigations of the Ethylene Tetramerisation Reaction", Journal of the American Chemical Society, 2005, 10723-10730, vol. 127, No. 30, American Chemical Society.

"Ready Biodegradability: 301 F Manometric Respirometry Test", Organization for Economic Cooperation and Development Guideline for Testing of Chemicals, adopted Jul. 17, 1992.

* cited by examiner

FUNCTIONALIZED LONG-CHAIN OLEFIN MIXTURES AND USES THEREFOR

BACKGROUND OF THE INVENTION

1. Technical Field

This invention relates to the field of functionalized olefins. More particularly, it relates to compositions and processes for preparing mixtures of functionalized olefins that may be useful as surfactants or as precursors for preparing surfactants.

2. Background of the Art

Surfactants are widely used in the chemical and manufacturing industries for a wide variety of purposes. These include, for example, imparting wettability and detergency in products including metal cleaning agents, paints, coatings, agricultural spread agents, and the like. The many types of surfactants are generally divided into four general classes—nonionic, anionic, cationic, and amphoteric—each of which offers certain advantages in certain uses. Each type, however, generally includes both a hydrophobic moiety and a hydrophilic moiety. One frequently-employed candidate for the hydrophobic portion of the surfactant molecule is an alcohol.

The value of an alcohol-derived surfactant is heavily dependent upon the characteristics of the starting alcohol. For example, the nature of the alcohol may be determinative of the surfactant's biodegradability, gelling tendency, rate of dissolution in water, and effective cloud point, each of which must be taken into consideration when selecting a surfactant for any given application. Alcohols may be natural or synthetic, but because of practical reasons including cost, product control, and limited availability of natural alcohol sources such as fats, oils and waxes, manufacturers have turned increasingly to synthesizing alcohols with an aim to using them to prepare surfactants.

For example, U.S. Pat. No. 6,963,014 B1 to Zeller et al. describes a process for preparing a C13-alcohol mixture comprising trimerizing a butane-containing C4-hydrocarbon stream containing less than 5 percent by weight of isobutene in the presence of a nickel-containing heterogeneous catalyst; isolating a C12-olefin fraction therefrom; hydroformylating the C12-olefin fraction; and then hydrogenating the product of the hydroformylation. The resultant alcohol mixture may be used to prepare surfactants via processes including alkoxylation, glycosidation, sulfation, phosphation, alkoxylation and subsequent sulfation, or alkoxylation and subsequent phosphation.

Other examples of alcohols synthesized from olefins include the invention represented by U.S. Publication US2004/0133037 A1 to Fenouil et al. This publication describes a process for preparing branched olefins by dehydrogenating an isoparaffinic composition over a suitable catalyst. The isoparaffinic composition is obtained by hydrocracking and hydroisomerization of a paraffinic wax. The produced olefins may be useful for making anionic, nonionic, or cationic surfactants, and in particular surfactant sulfates or sulfonates.

U.S. Pat. No. 6,433,207 B1 to Connor discloses a process for preparing branched olefins involving dimerization followed by an OXO process to form alcohols therefrom. This process claims to eliminate geminal branching, i.e., the elimination of "quaternary" carbon substitution. The resulting alcohols may be further processed to form surfactants.

U.S. Pat. No. 3,887,624 to Gipson et al. discloses vinylidene alcohols having unusually low melting points, that may be prepared by hydroformylation of vinylidene olefins (OXO process), followed by hydrogenation of the product of the hydroformylation. The vinylidene olefins are prepared by conventional dimerization of alpha olefins, mixtures thereof, and the like, such as that described in U.S. Pat. No. 2,695,327. The alpha olefins are prepared from the conventional conversion of ethylene by a combined-growth displacement reaction using a Ziegler-type polymerization catalyst such as a trialkylaluminum catalyst.

While these and a variety of other surfactant-ready alcohols are known in the art, there is still much room for new surfactants representing each of the four surfactant classes. Thus, processes for preparing new surfactant-ready alcohols also continue to be sought, to promote development of new surfactants that may offer improved performance, customization to specific applications, attractive cost, and a high level of environmental acceptance.

SUMMARY OF THE INVENTION

Accordingly, the present invention provides, in one aspect, a process for preparing a mixture of functionalized olefins comprising tetramerizing ethylene in the presence of a chromium-containing ethylene tetramerization catalyst such that a byproduct mixture of C10-C20 olefins is formed, and treating the byproduct mixture by a process selected from the group consisting of (i) OXO, such that at least a portion of the olefins is converted to an aldehyde; (ii) OXO/hydrogenation, such that at least a portion of the olefins is converted to an alcohol; (iii) OXO/amination, such that at least a portion of the olefins is converted to an alkyl amine; and (iv) sulfonation, such that at least a portion of the olefins is converted to an alpha olefin sulfonate.

The compositions prepared by the described processes are also described herein. These compositions, including aldehydes, alcohols, amines, amides, sulfates, sulfonates, sulfones, sulfides, sulfoxides, and combinations thereof, as well as derivatives thereof, offer potential for use as surfactants having desirable properties in a wide variety of applications.

DETAILED DESCRIPTION OF THE INVENTION

The process disclosed herein begins with a first mixture of olefins. This mixture is obtainable as the product stream that results from certain targeted higher olefin-producing processes, specifically processes that tetramerize ethylene to produce hexene and octene. Such a process includes use of a tetramerization catalyst that is based on chromium, and generally also elevated temperature.

The catalyst for preparing the first mixture may be any that is suitable for carrying out the desired tetramerization, and that has desirable selectivity for both 1-octene and 1-hexene. In one non-limiting embodiment, a chromium-based (Cr(III)) catalyst is selected, such as one exhibiting a PNP or PNNP configuration, that is, diphosphinoamine ligands with various substituents on both the N and P atoms. In certain particular and non-limiting embodiments, such may include polar-substituted diphosphinoamine ligands, wherein the polar groups are positioned on the aryl rings. Variation of ligand substitutions, such as, for example, heteroaromatic substituents, alkyl substituents such as ethyl, aromatic substituents such as cyclohexyl, or bulkier aromatic substituents such as biphenyl and naphthyl groups, each may alter the proportion of targeted products, but still be effective to produce a substantial yield for both the 1-octene and 1-hexene. Activation of the catalyst using an activator such as an aluminoxane or hydrogen may also be useful in ensuring desirable catalyst performance. Those skilled in the catalyst art will be aware of appropriate criteria for selecting specific catalysts and associated catalysis conditions of temperature and pressure. See, for example, A. Bollmann, et al., "Ethylene Tetramerization: A New Route to Produce 1-Octene in Exceptionally High Selectivities," *J. Am. Chem. Soc.,* 126(45),14712-14713, 2004; and M. J. Overett, et al., *J. Am. Chem. Soc.* 127 (2005), 10723; each of which is incorporated herein by reference in its entirety. The first mixture of olefins is prepared starting with an ethylene feedstock and using apparatus known to those skilled in the art to be useful for carrying out tetramerization. For example, in one non-limiting embodiment, an aluminoxane-activated chromium(III) catalyst system may be prepared in a Schlenk vessel, followed by transfer to a pressure reactor that is then charged with the ethylene. Other types of equipment, on various scales, may alternatively be selected. In general, optimization of the contact between the catalyst and the ethylene feedstock is desirable in order to facilitate the tetramerization reaction.

In one non-limiting embodiment, the tetramerization may be begun by preparing a suitable catalyst by adding diisopropylamine in toluene to a solution of $PCl_3$ in toluene at $-10°$ C., stirring for two hours, and then allowing the solution to warm to room temperature. After stirring for an additional hour, the solution may be filtered through a pad of celite. The product obtained after removal of the solvent is N,N-diisopropylphosphoramide dichloride, one example of a suitable catalyst.

Once a suitable catalyst is prepared or otherwise obtained, it may be used in the tetramerization reaction. For example, ethylene may be tetramerized using, as catalysts and activation agent, a combination of $CrCl_3$(tetrahydrofuran)$_3$, (phenyl)$_2$PN(pentyl)P(phenyl)$_2$ and methylaluminoxane (MAO). To accomplish this, in one non-limiting embodiment, a solution of the (phenyl)$_2$PN(pentyl)-P(phenyl)$_2$ in toluene may be added to a solution of the $CrCl_3$(tetrahydrofuran)$_3$ in toluene. The mixture is stirred and then transferred to an appropriate pressure reactor (autoclave) containing a mixture of toluene and the MAO at 60° C. The reactor is then charged with ethylene and the reactor temperature is thereafter controlled at 65° C., while maintaining the ethylene pressure at 30 bar gauge (barg), or approximately 31 atmospheres. The reaction is allowed to continue for 60 minutes, and then the ethylene feed is discontinued and the reactor is cooled to below 10° C. Excess ethylene is then released from the autoclave and the liquid within the autoclave is quenched with ethanol followed by 10 percent hydrochloric acid in water. The organic layer is dried over anhydrous soldium sulfate and then filtered to isolate the solid tetramerization products. Those skilled in the art will be well aware of other protocols, including in particular other catalysts and catalyst activators, as well as a variety of temperatures, pressures, and types of equipment, that may be conveniently and effectively used for the tetramerization.

The tetramerization products may include the targeted linear alpha olefins, notably 1-hexene and 1-octene, in a desirable yield of each. Such yield may be, in some non-limiting embodiments, equal to or greater than about 80 percent of theoretical, and in other non-limiting embodiments, equal to or greater than 85 percent of theoretical. The remainder may include other alpha olefins, mainly those of longer carbon chain lengths, which in many cases range from about C10 to about C20.

The portion containing the targeted 1-hexene and 1-octene may be conveniently separated from the portion containing the mixture of higher alpha olefins by conventional means such as, for example, distillation. It is this second, by-product mixture of higher alpha olefins that is the portion that is selected for further processing in the present invention. In certain non-limiting embodiments, one or more additional distillations may be carried out in order to include only the C10-C14 portions in the subsequently-employed processing, with the so-called "heavies," i.e., the C15-C20 constituents, thereby eliminated.

In some preferred embodiments, the C10-C14 portion used for further functionalization comprises about 40 to 61 weight percent of C12 fraction and about 39 to 60 weight percent of both C10 and C14 fractions. More preferably, the C10-C14 portion comprises about 19 to 25 weight percent of C10 fraction, about 45 to 61 weight percent of C12 fraction, and about 27 to 33 weight percent of C14 fraction. Further preferably, the C10-C14 portion comprises about 21 to 23 weight percent of the C10 fraction, about 47 to 49 weight percent of the C12 fraction, and about 29 to 31 weight percent of the C14 fraction.

It is further preferred, that the C10 fraction contains the following isomer distribution: about 20 to 45% by weight, more preferably about 30 to 42%, terminal linear decene; about 1 to 15%, more preferably about 5 to 11%, internal linear decenes, and with the remainder being branched decenes.

In a further preferred embodiment, the C10 fraction contains about 20 to about 45 weight % of linear decenes (which includes both terminal and internal olefins), with the remaining components being branched decenes.

It is also preferred that the C14 fraction contain the following isomer distribution: about 2 to 15%, more preferably about 5 to 15%, linear tetradecenes (which includes both terminal and internal olefins), with the remainder being branched tetradecenes.

Figure 1:
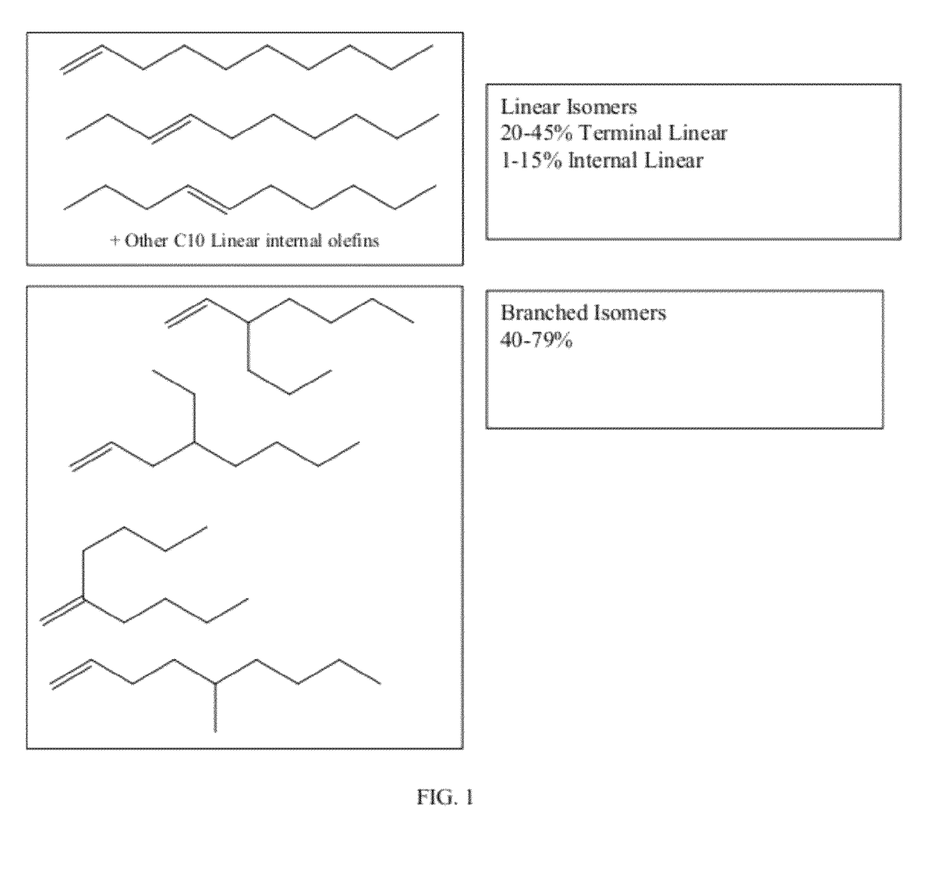
FIG. 1 provides a partial listing of linear and branched C10 isomers in a C10-C14 olefin stream.
Figure 2:
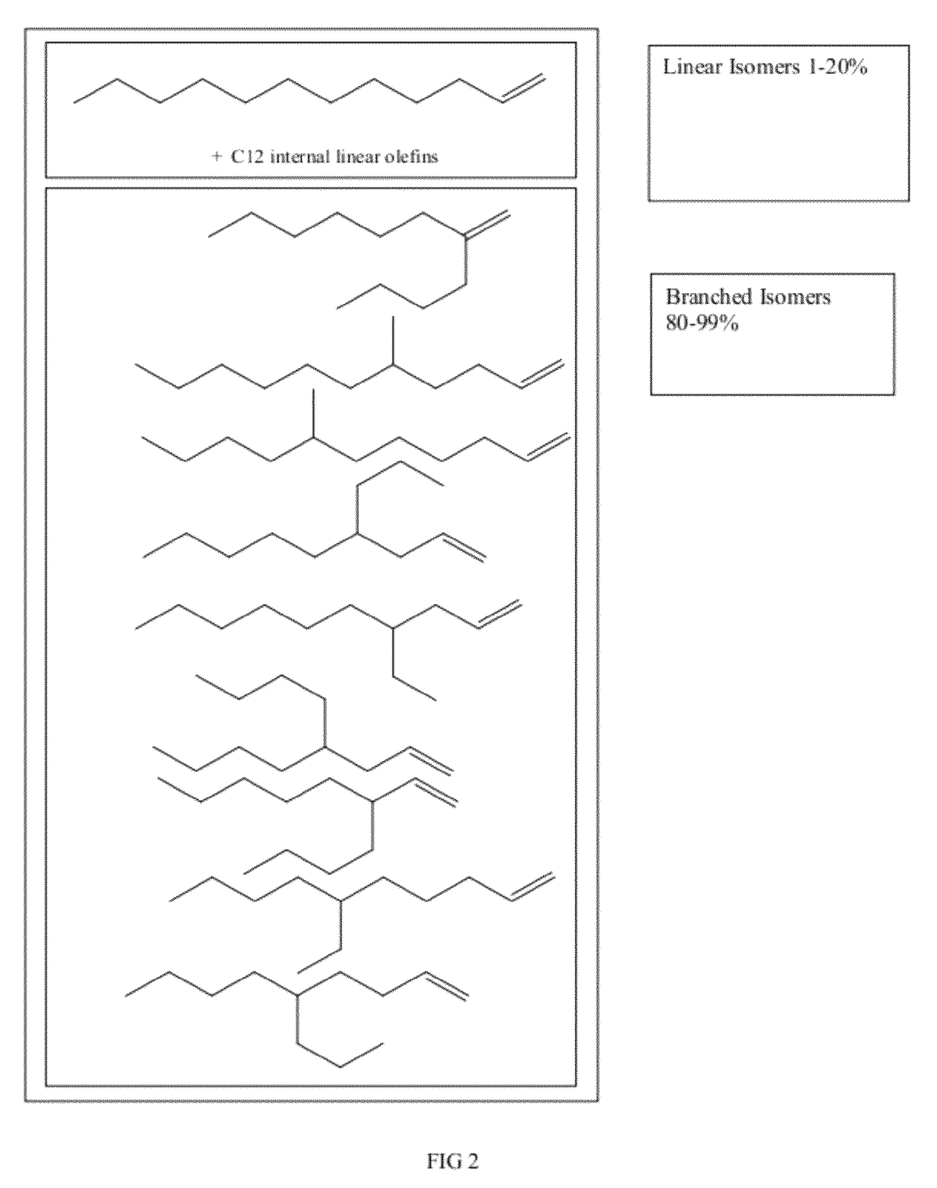
FIG. 2 provides a partial listing of linear and branched C12 isomers in a C10-C14 olefin stream.
Figure 3:
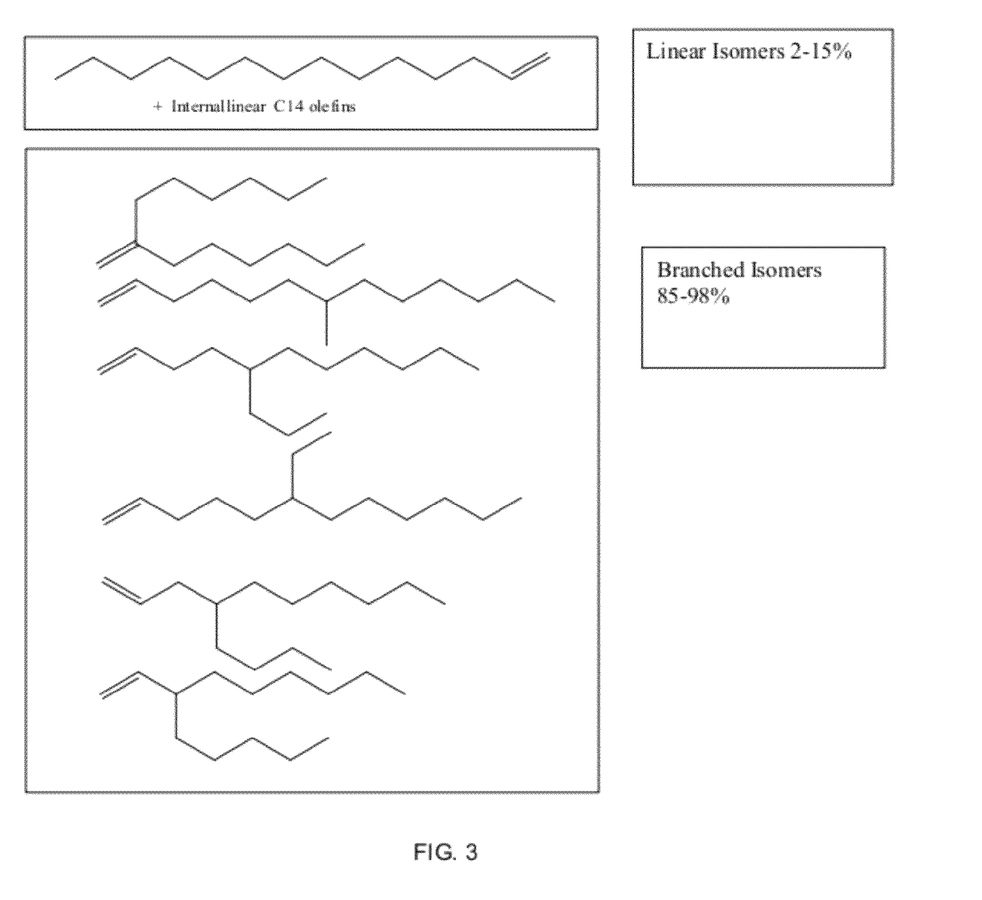
FIG. 3 provides a partial listing of linear and branched C14 isomers in a C10-C14 olefin stream.

The isomer distributions in the C10, C12, and C14 fractions, according to the foregoing preferred embodiments, are shown in FIGS. 1, 2, and 3. Some of the specific isomers within each group are also shown.

The second step in the inventive process accomplishes the functionalization of this by-product mixture. As defined herein, "to functionalize," in any of its forms, means to add a reactive functional group to a compound or mixture of compounds. Such a reactive functional group is generally selected from the group consisting of an aldehyde group, a hydroxyl group, an amide group, an amine group, a sulfide group, a sulfoxide group, a sulfone group, a sulfate group, a sulfonate group, or a combination thereof.

One way to functionalize the by-product mixture is via the so-called OXO process, wherein the mixture is treated by hydroformylation. Hydroformylation is defined as a reaction that involves adding hydrogen and carbon monoxide across a double bond to yield aldehyde products. In this particular functionalization of the by-product mixture, a subcategory of hydroformylation, referred to as the OXO process, involves treating the by-product mixture with a combination of hydrogen and carbon monoxide in the presence of a catalyst based on rhodium or another transition metal, such as cobalt, platinum, palladium, or ruthenium. The hydroformylation catalyst may be of homogeneous or heterogeneous type. Such catalysts may be prepared by methods well known in the art. In certain embodiments the catalyst for this hydroformylation is a metal-ligand complex catalyst.

In certain embodiments the metals which are included in the metal-ligand complex catalyst include Groups 8, 9 and 10 metals selected from rhodium (Rh), cobalt (Co), iridium (Ir), ruthenium (Ru), iron (Fe), nickel (Ni), palladium (Pd), platinum (Pt), osmium (Os), and mixtures thereof, with the preferred metals being palladium, rhodium, cobalt, iridium and ruthenium, more preferably palladium, rhodium, cobalt and ruthenium, and in certain particular and non-limiting embodiments, palladium. The ligands may include, for example, organophosphorus, organoarsenic and organoantimony ligands, and mixtures thereof, and in certain non-limiting embodiments organophosphorus ligands may be selected. These may include organophosphines, e.g., mono-, di-, tri- and poly-(organophosphines), and organophosphites, e.g., mono-, di-, tri- and poly-(organophosphites). Other suitable organophosphorus ligands may include, for example, organophosphonites, organophosphinites, amino phosphines and the like. Other suitable ligands include, for example, heteroatom-containing ligands, such as 2,2'-bipyridyl and the like. In some non-limiting embodiments rhodium-based metal-ligand complex catalysts which employ phosphorus based ligands or mixtures of ligands may be selected. In other non-limiting embodiments mixtures of such catalysts may be selected.

The concentrations of complexed ligand, metal, and catalyst in general in the hydroformylation reaction will depend upon selected constituents, reaction conditions and solvent employed. For example, in some embodiments the concentration of complexed ligand may range from about 0.005 to about 25 weight percent, based on total weight of the reaction mixture. In other particular and non-limiting embodiments, the complexed ligand concentration may range from about 0.01 to about 15 weight percent, and preferably from about 0.05 to about 10 weight percent, based on total weight of the reaction mixture. In general, the concentration of the metal may be from a few parts per million by weight to as high as about 2000 parts per million by weight or greater, based on the weight of the reaction mixture. In certain particular and non-limiting embodiments, the metal concentration may range from about 50 to about 1500 parts per million by weight, based on the weight of the reaction mixture, and more preferably is from about 70 to about 1200 parts per million by weight, based on the weight of the reaction mixture. Thus, the molar ratio of complexed ligand:metal may, in fact, range from about 0.5:1 to about 1000:1. In some non-limiting embodiments the overall concentration of catalyst in the reaction mixture may range from several parts per million to several percent, based on weight of the reaction mixture.

In addition to the metal-ligand complex catalyst, free ligand (i.e., ligand that is not complexed with the metal) may also be present in the hydroformylation reaction mixture. The free ligand may correspond to, for example, any of the ligands discussed hereinabove as employable herein. It is in some embodiments preferred that the free ligand be the same as the ligand of the metal-ligand complex catalyst employed, but such is not required. The hydroformylation reaction may involve up to 100 moles, or more, of free ligand per mole of metal in the hydroformylation reaction mixture. Preferably the hydroformylation reaction is carried out in the presence of from about 0.25 to about 50 moles of coordinatable phosphorus, and more preferably from about 0.5 to about 10 moles of coordinatable phosphorus per mole of metal present in the reaction medium, with the amounts of coordinatable phosphorus being the sum of both the amount of coordinatable phosphorus that is bound (complexed) to the palladium metal present and the amount of free (non-complexed) coordinatable phosphorus present. If desired, make-up or additional coordinatable phosphorus may be supplied to the reaction mixture at any time and in any suitable manner, for example, to maintain a predetermined level of free ligand in the reaction mixture.

The OXO process may be accomplished effectively, in certain non-limiting embodiments, under relatively high pressures (from subatmospheric to about 100 atmospheres) and at temperatures from about 40° C. to about 300° C., but a wider range of temperatures from about 10° C. to about 400° C. and pressures from about 10 psig to about 3000 psig may be employed, provided that the desired end result is achieved. This result is production of a mixture of aldehydes, each of which has one more carbon atom than the specific C10-C20 olefin from which it was made.

The product aldehydes may be separated from the hydroformylation mixture by conventional means such as vaporization or distillation. The aldehyde products may also be separated from the hydroformylation catalyst by phase separation. An example of such is where a phosphorus based ligand has been designed to preferentially phase separate into a polar or aqueous-polar phase, and consequentially the metal, e.g., rhodium, and ligand components may be readily recovered from the relatively non-polar aldehyde product mixture. Such aldehydes may be useful as surfactants themselves or as hydrophobes therefor, or they may be subjected to further processing to produce derivatives as discussed hereinbelow.

Such further processing may involve treatment of the mixture of aldehydes with hydrogen over a suitable hydrogenation catalyst to form the corresponding alcohols. Because the feed involves a mixture of olefins, the result will be a mixture of alcohols. This hydrogenation may be carried out using a variety of known hydrogenation catalysts in conventional amounts. Such catalysts may be homogeneous or heterogeneous in type, and may comprise a variety of metals, including but not limited to palladium, ruthenium, platinum, rhodium, copper chromite, nickel, copper, cobalt, other Groups 8, 9 and 10 metals, chromium oxide, a variety of metal nitrides and carbides, combinations thereof, and the like. These metal catalysts may be supported on a variety of supports, including titania, magnesium silicate, lanthanum oxide, ceria, silicon carbide, magnesium silicate, aluminas, silica-aluminas, vanadia, combinations thereof, and the like. The catalysts may be further promoted by additional metals or other additives, including, but not limited to, barium, manganese, zirconium, selenium, calcium, molybdenum, cobalt, other Groups 8, 9 and 10 metals, copper, iron, zinc, combinations thereof, and the like. A variety of homogeneous catalysts may also be employed, comprising, for example, rhodium, ruthenium, cobalt, nickel and the like. Such catalysts may be promoted or stabilized by a variety of ligands including nitrogen or phosphorus containing materials such as, but not limited to, amines, phosphines, phosphites, combinations thereof, and similar materials. Those skilled in the art will understand that any catalyst that is deemed to have sufficient catalytic activity to effect the desired result hereunder is intended to be comprehended hereby.

The hydrogenation may be carried out according to any known protocols and methods, and using conventional apparatus. For example, such may be done in a tubular or a stirred tank reactor. Effective reaction temperatures may range from about 50° C. to about 400° C. or higher, preferably from about 100° C. to about 300° C., for a period of from about 1 hour or less to about 4 hours or longer, with the longer times being in some embodiments employed in conjunction with the lower temperatures. Reaction pressures may range from 15 psig to about 3000 psig or greater. In certain preferred and non-limiting embodiments, mild temperatures and low pressures may be generally considered desirable in promoting acceptable catalyst performance and lifetime, as well as product stability. The amount of hydrogenation catalyst used is dependent on the particular hydrogenation catalyst employed and may range, in certain non-limiting embodiments, from about 0.01 weight percent or less to about 10 weight percent or greater, based on the total weight of the starting materials.

Once the alcohols are formed, they may be used as the hydrophobe portion of mixtures of compounds useful as surfactants. For example, they may be alkoxylated to form alkoxylates, such as, for example, ethoxylates. They may be sulfated to form the alcohol sulfates, or aminated via reductive amination. Those skilled in the surfactant arts will be well aware of the many practical uses of the alcohols produced via the combined OXO/hydrogenation reaction without further discussion herein.

If alkoxylation is selected, such process may be carried out in the presence of acidic or alkaline catalysts. It is preferred to use alkaline catalysts, such as hydroxides or alcoholates of sodium or potassium, including NaOH, KOH, sodium methoxide, potassium methoxide, sodium ethoxide and potassium ethoxide. Double metal cyanide (DMC) catalysts may also be used, as described in U.S. Patent Publication 2005/0170991, which is incorporated herein by reference in its entirety. Base catalysts are normally used in a concentration of from 0.05 percent to about 5 percent by weight, preferably about 0.1 percent to about 1 percent by weight based on starting material. In one non-limiting embodiment, a C10-16 mixture is first converted to an alcohol as described hereinabove, and subsequently converted to form a nonionic surfactant via alkoxylation with from 0 to about 10 moles of propylene oxide and from greater than about 0 to about 100 moles of ethylene oxide. In another embodiment the mixture treated with propylene oxide and ethylene oxide is a C10-20 mixture, and in still another embodiment the mixture is a C11-15 mixture.

The addition of alkylene oxides may, in one non-limiting embodiment, be carried out in an autoclave under pressures from about 10 psig to about 200 psig, preferably from about 60 to about 100 psig. The temperature of alkoxylation may range from about 30° C. to about 200° C., preferably from about 100° C. to about 160° C. After completion of oxide feeds, the product is typically allowed to react until the residual oxide is less than about 10 ppm. After cooling the reactor to an appropriate temperature ranging from about 20° C. to 130° C., the residual catalyst may be left unneutralized, or neutralized with organic acids, such as acetic, propionic, or citric acid. Alternatively, the product may be neutralized with inorganic acids, such as phosphoric acid or carbon dioxide. Residual catalyst may also be removed using ion exchange or an adsorption media, such as diatomaceous earth. In many non-limiting embodiments the resulting alkoxylated material may be an effective surfactant.

In another non-limiting embodiment, the by-product mixture of higher (C10-C20) olefins may be treated via a combined OXO/amination process, again involving a hydroformylation wherein an aldehyde functional group is incorporated in the higher alpha olefins, followed in this case by an amination step. Those skilled in the art will be aware that amination includes, but is not limited to, any process by which an amine functional group is introduced into an organic molecule, such as reaction with ammonia or another amine, and may include reductive amination. For example, a reductive amination may, in one non-limiting embodiment, be carried out using a rhodium catalyst, followed by hydrogenation (see, for example, U.S. Pat. No. 7,220,884 B1, which is incorporated herein by reference in its entirety). The amination reaction may be conducted at a temperature of from about 50° C. to about 300° C. The temperature is, in certain non-limiting embodiments, sufficient for reaction to occur (which may vary with the selected catalyst, free ligand, and/or promoter selected), but is desirably not sufficiently high to result in aldehyde decomposition or polymerization.

The amination reaction may be conducted over a wide range of pressures, in some embodiments ranging from about 20 psig to about 2000 psig and at a temperature ranging from about 50° C. to about 300° C. It is desirable in some embodiments to conduct the amination reaction at pressures of from about 100 psig to about 1000 psig. The amination reaction may be effected in the liquid or vapor states, or in combinations thereof. The total pressure under which the reaction may be carried out will depend on the catalyst system used. Hydrogen partial pressure may be selected and may help to maximize the lifetime of the hydrogenation catalyst.

While any effective aminating agent may be selected, ammonia is a convenient and relatively inexpensive choice. It may be used to aminate the aldehydes in any amount, but desirably is present in at least stoichiometric amount, and in certain non-limiting embodiments may be particularly effective in excess of stoichiometric. The selected aminating agent may be fed to the reactor in a variety of ways, such as, as a liquid or a gas, in solution in, for example, water, or as a salt, e.g., ammonium salt, in solution or in some other appropriate manner. Any excess may then be separated off after the amination is completed. In cases where the amination is reductive, for example, it is desirable to co-feed hydrogen gas, or some other source of hydrogen. The aldehyde mixture may be fed to the reactor in any convenient manner, such as in solution, or as a neat liquid, or in the gas phase. This amination may be carried out using a variety of known catalysts, which may include materials described hereinabove as also useful for hydrogenation catalysts. Subsequent reactions well known to those skilled in the art may then be employed to produce quaternary compounds, amine oxides, amides or amine ethoxylates, many of which may be useful as surfactants for a given application.

The third further-processing option for the by-product mixture of higher alpha olefins is direct sulfonation. Those skilled in the art will be aware that sulfonation includes, but is not limited to, any process by which a sulfonate functional group is introduced to the molecule, such as reaction with $SO_3$, oleum, or $SO_3$ complexes with amines, ethers, or phosphines. For example, a sulfonation may, in one non-limiting embodiment, be carried out using $SO_3$ diluted in air. See, for example, U.S. Pat. No. 4,102,911, which is incorporated herein by reference in its entirety. Other protocols will be familiar to those skilled in the art and may alternatively be employed. Generally, temperatures from about −50° C. to about 100° C. and pressures of from about 15 psig to about 200 psig may, in some non-limiting embodiments, be employed.

Those skilled in the art will readily see that the compounds resulting from the processes described hereinabove may serve as effective hydrophobes for further processing into surfactants, and that, in fact, many of the resultant functionalized compounds themselves may, without further processing, represent surfactants suitable for various applications. Such functionalized mixtures, with their reactivity and long carbon chain lengths, as well as other novel and desirable features, may offer improved properties as surfactants, where appropriate separation means such as distillation are employed, or as mixtures of surfactants. For example, it is noted in WO0042154, which is incorporated herein by reference in its entirety, that the backbone structure of a potential surfactant hydrophobe may be carried through to the derivative, with clear effect on performance. Similarly, EP 958267, incorporated herein by reference in its entirety, discusses the low temperature detergency and superior wetting efficiency of branched surfactant molecules. Such properties may include not only enhanced effectiveness as surfactants, but also reduced toxicity, increased biodegradability, decreased production cost, reduced production waste, and the like.

The description hereinabove is intended to be general and is not intended to be inclusive of all possible embodiments of the invention. Similarly, the examples hereinbelow are provided to be illustrative only and are not intended to define or limit the invention in any way. Those skilled in the art will be fully aware that other embodiments within the scope of the claims will be apparent, from consideration of the specification and/or practice of the invention as disclosed herein. Such other embodiments may include selections of specific catalysts; identification and proportions of starting and resulting compounds at each process step; mixing and reaction conditions, vessels, and protocols; performance and selectivity; applications of the final products; and the like; and those skilled in the art will recognize that such may be varied within the scope of the appended claims hereto.

EXAMPLES

Example 1

A tetramerization of ethylene is carried out using a dimethylpropylPNP (5 µmol) ligand together with Cr(acac)3 (5 µmol) as the catalyst system, 480 equivalents of MMAO-3A ( (multi-methyl aluminum oxide, a catalyst activator commonly used in polyolefin chemistry), methylcyclohexane as solvent, and reaction conditions of 45 bar pressure and 60° C. After rectification, a C10-C14 by-product fraction is produced. Estimates based on an isomer analysis of this fraction, using gas chromatography-mass spectroscopy (GC-MS), are shown in Table 1. The composition of the C12 fraction is extrapolated from the C10 and C14 estimates, as the isomer analysis is considered to be less than satisfactory in this region.

TABLE 1

|  | C10 | C12 | C14 |
|---|---|---|---|
| Approximate split (mass fraction of C10-C14 fraction) | 22% | 48% | 30% |
| Mass % identified | 90 | nd** | 95 |
| Mass % olefin | 98 | 99 | 99 |
| Min. mass % linear or branched, non-vinylidene α-olefin* | 72 | 72 | 72 |
| Min. mass % linear or methyl-branched non-vinylidene olefin* | 63 | 52 to 63 | 52 |
| Min. mass % linear or methyl-branched non-vinylidene α-olefin* | 53 | 50 to 54 | 51 |
| Min. mass % methyl-branched, non-vinylidene α-olefin* | 12 | 12 to 35 | 35 |

*These estimates are minimums, as some of the unidentified products are expected to increase these values.
**nd means no data available.

Several isomers are identified from the C10-C14 olefin fraction (see FIGS. 1-3). In these isomers the amount and type of branching varies between carbon chain lengths of the fraction. However, the linear α-olefin seems reduced from approximately 40 percent in the C10 fraction to about 10 percent in the C14 fraction.

Example 2

Isolation of C10-C14 Olefin Mixture

An olefin mixture (supplied by Sasol Technology, from its proprietary ethylene tetramerization process which includes using a chromium-based catalyst) containing C8-C32 olefins, is batch-distilled using a small scale glass distillation setup with 4-inch Vigreux column at 0.5-1.0 torr vacuum. The fraction that boils between about 60° C. and about 95° C. is collected and found to contain a combination of olefins in the C10-C14 range.

Hydroformylation of C10-C14 Olefin Mixture

Catalyst solution preparations and solution/olefins transfers are made under a nitrogen atmosphere. A catalyst solution is prepared from about 0.1894 grams $Rh(CO)_2$(acetylacetate), 19 milliliters of a solution of 21 percent by weight of dicyclohexylphenylphosphine-monosulfonate-sodium salt in N-methyl-pyrrolidinone (NMP), and 60 milliliters of NMP. The catalyst solution and about 123.5 grams of the C10-C14 olefin mixture is charged to a 500 milliliter magnetically stirred autoclave which has been purged with nitrogen. The reactor is pressurized/vented three times with 100 psig 1:1 $H_2$/CO. The autoclave is pressurized with 100 psig 1:1 $H_2$/CO and heated to 90° C. over about 10 minutes, after which the reactor is pressurized to 500 psig 1:1 $H_2$/CO. After about 3 hours and 15 minutes of reaction at 90° C. and 500 psig 1:1 $H_2$/CO, the reaction temperature is raised to about 100° C. The reaction is maintained at 100° C. under 500 psig 1:1 $H_2$/CO for an additional 16 hours and 30 minutes. The reaction is then cooled to approximately 23° C. Analysis of the reaction mixture by gas chromatography indicates that conversion of the olefin mixture to C11-C15 aldehydes is about 90 percent of theoretical.

Product/Catalyst Separation

A 500 milliliter separatory funnel is charged with about 207.9 grams of the aldehyde reaction mixture from the hydroformylation reaction described hereinabove, along with about 75 milliliters distilled water. The mixture is vigorously shaken and the layers allowed to separate. The bottom aqueous/NMP layer is drained and the reaction mixture is extracted again with 50 milliliters of distilled water. The combined aqueous/NMP layers weigh about 180.2 grams.

Hydrogenation of C11-C15 Aldehyde Mixture

RANEY 3110™ nickel catalyst is washed three times with isopropanol to remove any water. (RANEY 3110™ is a tradename of the Davison Chemical Company.) Approximately 8 grams of this catalyst, wet with isopropanol, is charged to the bottom of a 500 milliliter magnetically stirred autoclave along with about 151.2 grams of the organic aldehyde product from the extraction described hereinabove. The reactor is sealed and pressurized/vented three times with 50 psig $H_2$. The reactor is then pressurized to about 100 psig with $H_2$ and heated to 90° C. over 10 minutes, after which the reactor is pressurized to 500 psig $H_2$. After 1 hour of reaction at 90° C. and 500 psig $H_2$, the reaction temperature is raised to about 100° C. The reaction is maintained at 100° C. under 500 psig $H_2$, for an additional 5 hours. The reaction is cooled to about 2° C. Analysis of the reaction mixture by gas chromatography, $^1$H and $^{13}$C NMR indicates essentially complete conversion of the aldehyde mixture to C11-C15 alcohols.

Ethoxylation of the C11-C15 Alcohols

About 235.2 grams of the above-described C11-C15 alcohol mixture is catalyzed with about 1.42 grams of solid KOH (flake), and dehydrated under 30 mm Hg/nitrogen at about 100° C. for about 30 minutes. This material is then ethoxylated at about 130° C. with about 415 grams of ethylene oxide. After complete reaction, the mixture is neutralized at about 70° C. with about 0.9 g of acetic acid (to a pH of about 5.5). This material has a final cloud point (1 percent aqueous) of about 48° C. By mass balance, the composition of the final surfactant is the 7.7 mole ethoxylate of the C11-15 alcohol, i.e., C11-15(EO)7.7.

An additional sample is prepared by ethoxylating a 70:30 blend of C12-C14 linear alcohols with 7 moles of ethylene oxide. This sample is referred to as C12-C14(EO)7 and is a comparative sample.

Performance Comparison of the C11-C15 Ethoxylate

The performance of the 7.7 mole ethoxylate of the C11-C15 alcohol (C11-C15(EO)7.7) is compared with other well-known non-ionic surfactants with similar cloud points, including TERGITOL™ NP-9, which is identified by the manufacturer as nonylphenol (9) polyethoxylate; NEODOL™ 25-7, which is identified by the manufacturer as a seven mole ethoxylate of a C12-C15 primary alcohol; TERGITOL™ 15-S-9, which is identified by the manufacturer as a nine mole ethoxylate of a C11-C15 secondary alcohol, and the comparative C12-14(EO)7 sample. TERGITOL™ is a trademark of The Dow Chemical Company, and NEODOL™ is a trademark of Shell Chemical Company. The tests performed include:

A) Draves Wetting Test: American Association of Textile Chemists and Colorists (AATCC) Test 17, also identified as ASTM D2281. For this test solutions of the surfactant at varying concentrations (0.05 weight percent, 0.10 weight percent, and 0.15 weight percent) are prepared in deionized water. A cotton skein (40/2 combed peeler yarn from Testfabrics, Inc.) is then placed in each solution and elapsed time until the skein collapses is measured. In addition, the concentration of the surfactant required for wetting in 20 seconds is calculated, based on a linear regression of a log time versus log concentration plot that has been built on data from the 0.05 weight percent, 0.10 weight percent, and 0.15 weight percent solution tests using the cotton skein.

B) Ross-Miles Foam Height Test: This test is carried out according to the protocol of ASTM D1173.

C) Surface Tension and Critical Micelle Concentration (CMC) Measurement. For this test the surface tension of a surfactant-water solution is measured while incrementally adding the surfactant to de-ionized water. Results are measured in terms of dyne/centimeters using a Wilhelmy plate. Results are recorded versus surfactant concentration. The Critical Micelle Concentration is the point at which an increase in surfactant concentration no longer results in a change in surface tension.

D) Pour Point Test: This test is carried out according to the protocol of ASTM Test D97.

E) Dynamic Surface Tension: For this test the air/liquid surface tension, in dynes/cm at 100 milliseconds, of a 0.1 percent by weight solution of surfactant in water is measured using a Kruss BP-10 bubble tensiometer.

Data from Tests A-E is shown in Table 2 hereinbelow.

TABLE 2

| Sample | Surface Tension at 10 milliseconds | Draves Wetting | | | | | Surface Tension at 0.1 wt. % | Ross Miles Foam, 0.1% | |
|---|---|---|---|---|---|---|---|---|---|
| | | 0.05 wt % | 0.1 wt. % | 0.15 wt. % | 20 sec wet time | CMC** | | Initial, mm | Final, mm |
| C11-15(EO)7.7 | 58 | 39 | 13 | 8 | 0.08 | 15 | 29 | 102 | 54 |
| Tergitol NP-9* | 57 | 34 | 12 | 6 | 0.07 | 20 | 30 | 148 | 35 |
| Tergitol 15-S-9* | 50 | 36 | 14 | 7 | 0.08 | 61 | 28 | 172 | 40 |
| Neodol 25-7* | Not Determined | 63 | 22 | 13 | 0.11 | 11 | 27 | 105 | 100 |
| C12-14(EO)7* | 57 | 36 | 11 | 9 | 0.07 | 18 | 29 | 110 | 100 |

*indicates not an example of the invention.
**Critical Micelle Concentration

F) Laundry testing is carried out using a Terg-O-Meter with test conditions as follows: agitation rate=100 cycles/minute; wash temperature=40° C.; wash bath size=1 L; polyester/cotton swatches 3-in. by 3-in. (7.5-cm by 7.5-cm) square, with pinked edges, using Sebum/Pigment (STC EMPA 119) from Testfabrics, Inc. The fabric swatches are washed using de-ionized water with 300 ppm of the identified surfactant. The delta reflectance is then measured using a Hunter Colorimeter in the "reflectance" mode. Larger values of "delta reflectance" correspond to greater degrees of cleaning.

Data from Test F is shown in Table 3 hereinbelow.

TABLE 3

| Sample | Delta Reflectance |
|---|---|
| Water* | −0.5 (+/−0.7)** |
| Tergitol NP-9* | 9.8 (+/−3.1) |
| Tergitol 15-S-9* | 7.4 (+/−2.4) |
| C11-C15(EO)8 | 7.1 (+/−2.37) |

*indicates not an example of the invention.
**the error readings represent the 90 percent confidence interval.

G) The biodegradability of the C11-C15(EO)7.7 ethoxylate according to the invention is tested by exposing the C11-15 ethoxylate to microorganisms derived from activated sludge obtained from a municipal sewage treatment plant under aerobic static exposure conditions, using standard OECD 301 F methodology. OECD 301 F refers to the Organisation for Economic Cooperation and Development Guidelines for the Testing of Chemicals, "Ready Biodegradability: Manometric Respirometry Test," Procedure 301 F, adopted 17 Jul. 1992, which is incorporated herein by reference in its entirety. Data from Test G is shown in Table 4 hereinbelow:

TABLE 4

| Time (days) | Test 1 Degradation, % | Test 2 (duplicate) degradation, % | Mean Degradation (%) |
|---|---|---|---|
| 0 | 0 | 0 | 0.0 |
| 1 | 4 | 0.8 | 2.4 |
| 2 | 12.7 | 17.4 | 15.1 |
| 3 | 22.1 | 22.1 | 22.1 |
| 4 | 27.7 | 26.1 | 26.9 |
| 5 | 38.7 | 35.5 | 37.1 |
| 6 | 44.2 | 44.2 | 44.2 |
| 7 | 50.5 | 48.9 | 49.7 |
| 8 | 55.3 | 53.7 | 54.5 |
| 9 | 56.9 | 55.3 | 56.1 |
| 10 | 57.6 | 57.6 | 57.6 |
| 11 | 60.8 | 60.8 | 60.8 |
| 12 | 62.4 | 64 | 63.2 |
| 13 | 66.3 | 64.8 | 65.6 |
| 14 | 68.8 | 65.5 | 67.2 |
| 15 | 70.4 | 68.8 | 69.6 |
| 16 | 70.4 | 70.4 | 70.4 |
| 17 | 72.7 | 69.6 | 71.2 |
| 18 | 72.7 | 71.2 | 72.0 |
| 19 | 72.7 | 72.7 | 72.7 |
| 20 | 74.3 | 72.7 | 73.5 |
| 21 | 73.5 | 73.5 | 73.5 |
| 22 | 72.7 | 74.3 | 73.5 |
| 23 | 72 | 75.1 | 73.6 |
| 24 | 74.3 | 75.9 | 75.1 |
| 25 | 73.5 | 76.7 | 75.1 |
| 26 | 75.1 | 76.7 | 75.9 |
| 27 | 72.7 | 77.5 | 75.1 |
| 28 | 74.3 | 77.5 | 75.9 |

Test results show that the C11-C15(EO)7.7 ethoxylate exhibits "ready biodegradability" as defined by OECD 301 F, that is, it shows greater than 60 percent biodegradation in 28 days in all of the aerobic mineral salt nutrient media. Notably, it reaches more than 60 percent biodegradation within 10 days after reaching 10 percent biodegradation.

What is claimed is:

1. A surfactant composition comprising an aldehyde, an alcohol, an amine, an amide, a sulfate, a sulfonate, a sulfone, a sulfide, a sulfoxide, or a combination thereof, prepared by a process comprising tetramerizing ethylene in the presence of a chromium-containing ethylene tetramerization catalyst to form 1-hexene, 1-octene, and a byproduct mixture comprising C10-C20 olefins, separating the 1-hexene and 1-octene from the byproduct mixture wherein after separation from the 1-hexene and 1-octene, the byproduct mixture is distilled to separate therefrom a second byproduct mixture of C10-C14 olefins consisting of a C10, a C12, and a C14 fraction of olefins, and wherein the C10 fraction is from 40 to 79% branched isomers of the following structures:

the C12 fraction is from 80 to 99% branched isomers of the following structures:

and the C14 fraction is from 85 to 98% branched isomers of the following structures:

and treating the second byproduct mixture by a process selected from the group consisting of (i) OXO, such that at least a portion of the olefins is converted to an aldehyde; (ii) OXO/hydrogenation, such that at least a portion of the olefins is converted to an alcohol; (iii) OXO/amination, such that at least a portion of the olefins is converted to an alkyl amine; and (iv) sulfonation, such that at least a portion of the olefins is converted to an alpha olefin sulfonate.

2. The composition of claim 1 wherein the OXO process is carried out at a pressure of from about 15 psig to about 1500 psig and at a temperature from about 40° C. to about 300° C.

3. The composition of claim 1 wherein the hydrogenation is carried out at a pressure of from about 15 psig to about 3,000 psig and at a temperature from about 50° C. to about 400° C.

4. The composition of claim 1 wherein the alcohol is subsequently alkoxylated.

5. The composition of claim 1 wherein the amination is carried out at a pressure of from about 20 psig to about 2,000 psig and at a temperature from about −50° C. to about 300° C.

6. The composition of claim 1 wherein the sulfonation process is carried out at a pressure of from about 15 psig to about 200 psig and at a temperature from about −50° C. to about 100° C.

7. The composition of claim 1, which exhibits greater than about 60 percent biodegradation within 28 days according to OECD 301 testing criteria, and which further attains about 60 percent biodegradation within 10 days after reaching 10 percent biodegradation.

8. A surfactant composition comprising an aldehyde, an alcohol, an amine, an amide, a sulfate, a sulfonate, a sulfone, a sulfide, a sulfoxide, or a combination thereof, prepared by a process comprising
   treating a C10-C14 olefin mixture with a process selected from the group consisting of (i) OXO, such that at least a portion of the olefins is converted to an aldehyde; (ii) OXO/hydrogenation, such that at least a portion of the olefins is converted to an alcohol; (iii) OXO/amination, such that at least a portion of the olefins is converted to an alkyl amine; and (iv) sulfonation, such that at least a portion of the olefins is converted to an alpha olefin sulfonate
   wherein the C10-C14 olefin mixture consists of about 40 to about 61 weight percent of C12 fraction and about 39 to about 60 weight percent of both C10 and C14 fractions, and wherein the C10 fraction is from 40 to 79% branched isomers of the following structures:

the C12 fraction is from 80 to 99% branched isomers of the following structures:

and the C14 fraction is from 85 to 98% branched isomers of the following structures:

9. A surfactant composition according to claim 8 wherein the C10 fraction is:
   about 20 to about 45 weight percent terminal linear decene;
   about 1 to about 15 weight percent internal linear decenes; and
   balance branched decenes.

10. A surfactant composition according to claim 8 wherein the C10 fraction is:
    about 20 to about 45 weight percent of terminal and internal linear decenes; and
    balance branched decenes.

11. A surfactant composition according to claim 8 wherein the C14 fraction is:
    about 2 to about 15 weight percent terminal and internal tetradecenes; and
    balance branched tetradecenes.

* * * * *